United States Patent [19]

Vanderslice et al.

[11] Patent Number: 4,713,449
[45] Date of Patent: Dec. 15, 1987

[54] POLYSACCHARIDE POLYMER MADE BY XANTHOMONAS

[75] Inventors: Rebecca W. Vanderslice; Shannon, Patrick, both of Boulder, Colo.

[73] Assignee: Getty Scientific Development Company, Houston, Tex.

[21] Appl. No.: 762,878

[22] Filed: Aug. 6, 1985

[51] Int. Cl.$^4$ .................... C08B 37/00; C08B 37/18
[52] U.S. Cl. .................................. 536/123; 514/54; 536/114; 435/104; 252/8.551
[58] Field of Search .................... 536/114; 514/54; 536/123

[56] References Cited

U.S. PATENT DOCUMENTS

| | | | |
|---|---|---|---|
| 3,020,206 | 2/1962 | Patton et al. | 536/123 |
| 3,054,689 | 9/1962 | Jeanes et al. | 536/123 |
| 3,711,462 | 1/1973 | Abdo | 536/123 |
| 4,517,101 | 5/1985 | Williams et al. | 536/114 |

OTHER PUBLICATIONS

Ielpi, L., Couso, R., and Dankert, M., "Lipid Linked Intermediates in the Biosynthesis of Xanthan Gum," FEBS Letters, 130:253–256, (1981).
Ielpi, L., Couso, R., and Dankert, M. A., "Xanthan Gum Biosynthesis Pyruvic Acid Acetal Residues are Transferred from Phosphoenol Pyruvate to the Pentasaccharide-P-PLipid." Biochem. Biophys. Res. Comm., 102:1400–1408, (1981).
Ielpi, L., Couso, R., and Dankert, M. A., "Xanthan Gum Biosynthesis Acetylation Occurs at the Prenyl-Phospho-Sugar Stage," Biochem. Intern., 6:323–333, (1983).
Osborn, M. J. and Weiner, I. M., "Biosynthesis of a Bacterial Lipopolysaccharide." J. Biol. Chem., 243:2631–2639, (1967).
Colvin, J. R., Chene, L., Sowden, L. C., and Takai, M., "Purification and Properties of a Soluble Polymer of Glucose from Cultures of Acetobacter zylinum," Can. J. Biochem., 55:1057–1063, (1977).
Johnson, J. G. and Wilson, D. B., "Role of a Sugar-Lipid Intermediate in Colanic Acid Synthesis by Escherichia coli," J. Bact., 129:225–236, (1977).

Primary Examiner—Ronald W. Griffin
Attorney, Agent, or Firm—Finnegan, Henderson, Farabow, Garrett & Dunner

[57] ABSTRACT

A polysaccharide polymer is disclosed which is a better viscosifier of water than xanthan gum. The polysaccharide polymer and its non-acetylated form, are comprised of glucose and mannose moieties in a ratio of about 2:1. The invention also discloses Xanthomonas mutants which produce the polysaccharide polymer but which do not produce xanthan gum. Methods of preparing the polysaccharide polymers and of their use are also described.

5 Claims, 5 Drawing Figures

POLYSACCHARIDE POLYMER MADE BY XANTHOMONAS

BACKGROUND OF THE INVENTION

Xanthan gum is produced by bacteria of the genus Xanthomonas, such as the species campestris, albilineans, fragaria, vesicatoria, and the like. Xanthan gum is a widely used product due to its unusual physical properties: extremely high specific viscosity and pseudoplasticity. It is commonly used in foods as a thickening agent and in secondary oil recovery as mobility control and profile modification agents and in petroleum drilling fluids.

Chemically, xanthn gum is an anionic heteropolysaccharide. The repeating unit of the polymer is a pentamer composed of five sugar moieties: two glucose, one glucuronic acid and two mannose moieties. They are arranged such that the glucose moieties form the backbone of the polymer chain, and side chains of mannose-glucuronic acidmannose generally extend from alternate glucose moieties. Often this basic structure is specifically acetylated and/or pyruvylated. (Janson, P. E., Kenne, L., and Lindberg, B., Carbohydrate Research, 45, 275–282 (1975); Melton, L. D., Mindt, L., Rees, D. A., and Sanderson, G. R., Carbohydrate Research, 46, 245–257 (1976).) This and all other publications referred to herein are specifically incorporated by reference. The structure is depicted below:

SUMMARY OF THE INVENTION

It is an object of the present invention to provide a polysaccharide polymer which is a better viscosifier of water than naturally occurring xanthan gum.

It is a further object of this invention to provide a polysaccharide polymer having improved rheological properties over naturally occurring xanthan gum at elevated temperature and/or in the presence of salts.

It is a further object of the present invention to provide a microorganism having the ability to produce the polysaccharide polymer.

It is a further object of the invention to provide a process for preparing the polysaccharide polymer by aerobically fermenting a microorganism having the ability to produce the polysaccharide polymer.

In accordance with this invention, there is provided a composition comprising a polysaccharide polymer containing essentially no glucuronic acid moieties having a D-glucose:D-mannose ratio of about 2:1, wherein the D-glucose moieties are linked in a beta-[1,4] configuration to form the polymer backbone, and the D-mannose moieties are each linked in an alpha-[1,3] configuration generally to alternate glucose moieties. The invention also contemplates processes for making the polysaccharide polymer, microorganisms which make the polysaccharide polymer, and methods of using the polysaccharide polymer.

The polysaccharide polymer of this invention can be

In spite of the broad utility of naturally occurring xanthan gum, there are some situations where its physical properties become limiting. In particular, in secondary oil recovery it is not uncommon for the temperature of the oil-bearing reservoir and salt concentrations in the reservoir brine to be higher than are optimal for xanthan solutions. When these conditions occur, xanthan can precipitate, flocculate and/or lose viscosity. Therefore there is a need for new viscosifying products which perform well at high temperature and high salt conditions.

made by blocking one of the steps in xanthan gum biosynthesis. Therefore, rather than having a three-sugar side-chain extending from the backbone of beta-[1,4]-D-glucose as in xanthan gum, the polysaccharide polymer of this invention has a single sugar moiety generally linked to alternate glucose moieties of the backbone. The polysaccharide polymer of this invention is therein termed "polytrimer" because it consists of a repeating trimer unit, glucose-glucose-mannose. Its structure is shown below, where n is the number of repeating units in the polymer.

As shown by the above, the polytrimer consists of D-mannose linked alpha-[1,3] generally to alternate moieties of beta-[1,4] linked D-glucose. As in xanthan gum, an acetic acid moiety can be, but is not always, esterified at the 6-O position of mannose, as described in Sutherland, I. W., Carbohydrate Polymers, 1, 107-115, (1981). Although the structure of the polysacchride polymer is thought to be as shown, it is possible that under certain conditions of synthesis, a mannose moiety may not always be linked at alternating glucose residues.

BRIEF DESCRIPTION OF THE DRAWINGS

FIG. 1 depicts the assumed pathway of xanthan gum biosynthesis. It is based on the data of several laboratories. See, Ielpi, L., Couso, R. O., and Dankert, M. A., Biochem. Biophy. Res. Comm., 102, 1400-1408 (1981), FEBS Letters, 130, 253-256 (1981), Biochem. Intern., 6, 323-333 (1983); Osborn, M. J. and Weiner, I. M., J. Biol. Chem., 243, 2631-2639 (1967); Troy, F. A., Annual Reviews of Microbiology, 33, 519-560 (1979). Abbreviations used are: glu=glucose, gluA=glucuronic acid, man=mannose, glu-glu=cellobiose, P=phosphate, PP=pyrophosphate, C55=isoprenoid lipid carrier, PEP=phosphoenolpyruvate, AcCoA=acetyl coenzyme A, I-V=glycosyltransferases, UDP=uridine 5'-disphosphate, GDP=guanosine 5'-diphosphate.

DETAILED DESCRIPTION OF THE INVENTION

The polysaccharide polymer of this invention can be made with a cell-free enzyme system or can be made by growing cells of an appropriate mutant strain. Other means of preparing the polysaccharide polymer are also described below.

Figure 1:
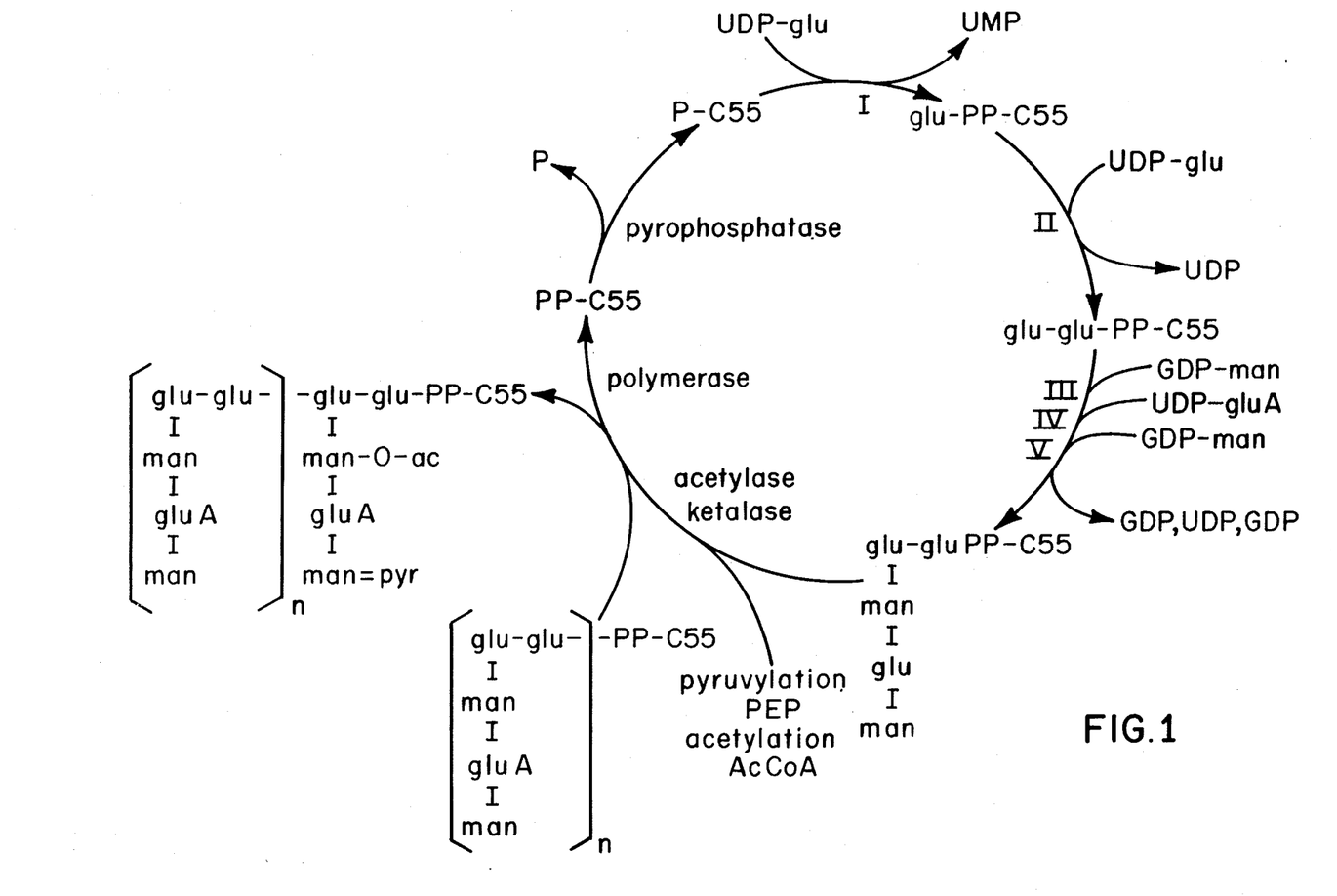

The basic method relating to use of a cell-free system to make xanthan gum is described in Ielpi, L., Couso, R. O., and Dankert, M. A. (FEBS Letters, 130, 253-256, (1981)) and can also be employed to make the polysaccharide polymer of this invention. For example, wild-type Xanthomonas campestris cells can be lysed by a freeze-thaw process and the substrates for polytrimer synthesis, UDP-glucose and GDP-mannose, with or without acetyl-CoA, can be added to the lysate. Alternate means of lysis may be used including but not limited to sonication, detergent treatment, enzyme treatment and combinations thereof. The lysate may be used in its crude form, or purification of the enzymes may be employed. The enzymes of the xanthan gum biosynthetic pathway covalently join the glucose and mannose moieties as in the normal pathway. Since the enzymes have no UDP-glucuronic acid to add to the nascent chains, the pathway is blocked at reaction IV (see pathway, FIG. 1,) and the intermediate isoprenoid lipid-pyrophosphate-glucose-glucose-mannose accumulates. Surprisingly, the xanthan polymerase which ordinarily acts on lipid-linked pentamer (glucose-glucose-mannose-glucuronic acid-mannose) is able to polymerize lipid-linked trimer, (glucose-glucose-mannose.) Thus, the polytrimer of the present invention can be synthesized in vitro.

The cell-free synthesis of polytrimer described above shows that Xanthomonas campestris cells have all the enzymes necessary to synthesize polytrimer. However, to use whole cells to synthesize polytrimer in vivo, a means of blocking xanthan gum synthesis at reaction IV (see FIG. 1) is required. Mutagenesis can be employed to block reaction IV.

Transposons, including but not limited to Tn10 and Tn903, can be used to mutagenize Xanthomonas. These transposons confer resistance to tetracycline and kanamycin, respectively. Transposons have the ability to insert themselves into genes; when they do so, they cause mutations by interrupting the coding sequence, (Kleckner, N., Annual Reviews of Genetics, 15, 341 (1981).) The transposons can be introduced into Xanthomonas on a so-called suicide vector, such as pRK2013. This vector has the ability to transfer itself into nonenteric bacteria, such as Xanthomonas, but cannot maintain itself (replicate) in that host, (Ditta, G., Corbin, D., Helinski, D. R., Proc. Natl. Acad. Sci. USA, 77, 7347-7351 (1980). Thus, if the suicide vector is introduced into a population of Xanthomonas cells, and that population is subsequently challenged with either tetracycline or kanamycin, the individuals which survive are those in which one of the transposons has inserted itself into the genome of Xanthomonas. Survivors of such a challenge can be screened for those which have lost the ability to make xanthan gum. Such mutants appear less mucoid than wild-type Xanthomonas.

In other embodiments of the invention, other means of mutagenesis can be employed to generate mutants which have lost the ability to make xanthan gum. Such means will readily occur to one skilled in the art, and include, without limitation, irradiation, recombinant DNA technology, and chemical mutagen treatment (Miller, J. H., Experiments in Molecular Genetics (1972); Davis, R. W., Botstein, D., and Roth, J. R., Advanced Bacterial Genetics (1980); Maniatis, T., Fritsch, E. F., Sambrook, J., Molecular Cloning (1982), Cold Spring Harbor).

Although mutants can first be chosen which appear less mucoid than wild-type, those desired retain the ability to make some polysaccharide. Cell-free extracts of each of the xanthan gum deficient mutants can be prepared and tested by adding different combinations of substrates and analyzing the products. For example, if UDP-glucose, GDP-mannose, and UDP-glucuronic acid are added as substrates, the product should be identical to that produced when UDP-glucose and GDP-mannose are added. Alternatively, appropriate mutants can be detected by assaying the culture broth of each mutant for the presence of polytrimer. Thus xanthan gum deficient mutants can be found which appear to be blocked at reaction IV of the xanthan gum pathway. A mutant of this description has been placed on file at the American Type Culture Collection, Rockville, Md., as ATCC No. 53195. Such mutants can be used to synthesize polytrimer in vivo.

Although glycosyltransferase IV mutants have been employed in the examples to make the polytrimer of the present invention, other embodiments of the invention contemplate use of mutants in UDP-glucuronic acid metabolism. Such a mutant has been isolated and deposited at the American Type Culture Collection, Rockville, Md., under the ATCC No. 53196.

It is not beyond the scope of the invention to employ an enzyme inhibitor of wild-type glycosyltransferase IV or of UDP-glucuronic acid biosynthesis to arrive at the same product. Still other alternatives for producing polytrimer are contemplated including enzymatic and chemical degradation of natural xanthan gum as, for example, by removing the terminal mannose and glucuronic acid moieties from the side chains of xanthan gum.

Using similar schemes to mutagenize strains of Xanthomonas, it is possible to obtain mutants which produce other new polysaccharide polymers. For example, a mutation in the acetylase gene yields completely non-acetylated xanthan gum. When an acetylase mutation and a glycosyltransferase IV mutation are put in the same strain (a double mutant), a non-acetylaled polytrimer is produced. Other mutations and combinations of mutations of the xanthan pathway are possible to yield new products.

The mutants can be grown under conditions known in the art for growth of wild-type Xanthomonas. For example, they can be grown on suitable assimilable carbon sources such as glucose, sucrose, maltose, starch, invert sugar, complex carbohydrates such as molasses or corn syrup, various organic acids and the like. Mixtures of carbon sources can also be employed. The concentration of carbon source supplied is often between about 10 and 50 grams per liter. Also necessary for growth are an assimilable source of organic or inorganic nitrogen, generally between about 0.1 and 1.0 grams per liter, and minerals, the choice of which are easily within the skill of the art. Examples of suitable nitrogen sources are ammonium salts, nitrate, urea, yeast extract, peptone, or other hydrolyzed proteinaceous materials or mixtures thereof. Examples of suitable minerals include phosphorous, sulfur, potassium, sodium, iron, magnesium; these are often added with a chelating agent such as EDTA or citric acid.

Optimal temperatures for growth of Xanthomonas generally are between about 18° and 35° C., preferably between about 28° and 32° C. Xanthomonas cells are grown aerobically by supplying air or oxygen so that an adequate level of dissolved oxygen is maintained, for example, above about 10% of saturation. Preferably the level is kept above about 20%. The pH often is maintained at about 6.0 to 8.0, preferably at about 6.5 to 7.5.

The polysaccharide polymer of the present invention can be recovered from fermentation broths by a suitable means. Precipitation with isopropanol, ethanol or other suitable alcohol readily yields the polytrimer gum. Generally, alcohols are added to a concentration of about 50 to 75%, on the basis of volume, preferably in the presence of potassium chloride, sodium chloride or other salt. Alternatively, the polymer can be recovered from the broth by ultrafiltration.

When chemical analyses are performed on polytrimer gum to determine the ratio of glucose:mannose, a variation from the theoretical value of 2:1 is found. The same type of variation is found when analyzing xanthan gum. Measured ranges of the ratio of glucose:mannose will generally be between about 1.4:1 and about 2.4:1. Preferably the ratio will be between 1.7:1 and 2.1:1.

Levels of acetylation of the mannose residues of the polysaccharide polymer vary. In addition, it is not beyond the scope of the invention to employ a microorganism to make the polysaccharide polymer which is incapable of acetylating the mannose residue, such as acetylase-deficient mutants. In such a case there will be no acetylated mannose residues in the polysaccharide polymer.

Typically, concentrations of polytrimer in the fermentation broth are about 0.1% (w/w). Routine testing of fermentation conditions and classical and recombinant DNA strain improvement techniques, all within the skill of the art, can be employed to improve the yield.

On a weight basis, polytrimer is superior to xanthan as a viscosifier of an aqueous medium. The viscosity of solutions of polytrimer is retained at conditions of high temperatures and/or high salinity. Such solutions can be prepared at any desirable concentrations, preferably between about 0.01% and about 15%, by dissolving the polysaccharide polymer in an aqueous medium. The product of this invention is ideally suited for use in secondary oil recovery. The same techniques as are used with xanthan gum in the art, and are well-known in secondary oil recovery, are appropriate with the polysaccharide polymer. See, for example, Lindblom, G. P., et al., U.S. Pat. No. 3,198,268.

Mobility control solutions for use in enhanced oil recovery can be prepared from the polysaccharide polymer. Concentrations of from about 100 to about 3,000 ppm of the polysaccharide polymer are appropriate for such mobility control solutions. Other known additives may also be used in, or in combination with, these solutions to further enhance oil recovery. Such additives include, for example, surfactants and alkaline agents.

The polysaccharide polymer, like xanthan gum, can also be used as a thickening agent in foods, cosmetics, medicinal formulations, paper sizings, drilling muds, printing inks, and the like. In addition it can be used to reduce frictional drag of fluid flow in pipes.

The following examples are provided by way of exemplification and are not intended to limit the scope of the invention.

EXAMPLE 1

This example shows how the product of the present invention can be prepared in vitro, and identifies it as a truncated product of the xanthan pathway.

Preparation of Lysates

*Xanthomonas campestris* B1459 S4-L was obtained from Northern Regional Research Laboratories of the U.S. Department of Agriculture. Bacteria were grown in YM (yeast-malt medium) supplemented with 2% (w/v) glucose as described by Jeanes, A., et al. (U.S. Department of Agriculture, ARS-NC-51, 14 pp (1976)). Cultures were grown to late log phase at 30° C. at 300 rpm. The cells were titered on YM plus 2% (w/v) glucose plates at 30° C. The cells were harvested by centrifugation and washed with cold Tris-HCl, 70 mM, pH 8.2 Washed cells were resuspended in Tris-HCl, 70 mM, pH 8.2 with 10 mM EDTA and were freeze-thawed three times by a procedure similar to Garcia, R. C., et al. (European Journal of Biochemistry 43, 93–105, (1974)). This procedure ruptured the cells, as was evidenced by the increased viscosity of the suspensions and the complete loss of cell viability (one in $10^6$ survivors) after this treatment. The freeze-thawed lysates were frozen in aliquots at −80° C. Protein concentration was determined with BIO RAD assay (BIO RAD Laboratories, Richmond, Calif.) and was found to be 5 to 7 mg cell protein per ml of lysate.

Biosynthetic Assay Procedure

As described in Ielpi, L., Couso, R. O., and Dankert, M. A., FEBS Letters, 130, 253–256 (1981), an aliquot of freeze-thawed lysate (equivalent to 300 to 400 ug protein), DNAase I (10 ug/ml), and $MgCl_2$ (8 mM) were preincubated at 20° C. for twenty minutes. An equal volume of 70 mM Tris-HCl, pH 8.2, with the desired radiolabeled sugar nucleotides (UDP-glucose and GDP-mannose), with or without UDP-glucuronic acid, was added and incubated at 20° C. At various times, the reactions were stopped by the addition of EDTA to 4 mM. The samples were centrifuged; the pellets were washed two times with buffer. The supernatants were combined, carrier xanthan (100 ug) was added, and the xanthan plus synthesized polymer were precipitated with ethanol(60%)-KCl(0.8%). The precipitated polymer was resuspended in water and reprecipitated two more times to remove unincorporated label. Radioactivity incorporated into the gum fraction was determined in a liquid scintillation counter, and the data were processed to obtain incorporation in terms of pmoles.

TABLE 1

Incorporation of labeled sugars by freeze-thaw cell lysate of *X. campestris* B1459 S4-L into gum

| Incubation Mix | Gum Fraction (pmol) | | |
|---|---|---|---|
| | [$^3$H]man | [$^{14}$C]glc | glc/man |
| +UDPG, GDPM | 98 | 201 | 2.1 |
| +UDPG, GDPM, UDP-GA | 1540 | 1562 | 1.0 |
| dpm/pmol $^3$H = 442 | | | |
| $^{14}$C = 37.5 | | | |

UDPG = UDP-glucose
GDPM = GDP-mannose
UDP-GA = UDP-glucuronic acid
dpm = disintegrations per minute
pmol = picomole
glc = glucose
man = mannose
Cell lysates of B1459 S4-L were incubated at 20° C. for 30 minutes and processed to give the gum fractions as described in the text. The molar ratio of glucose to mannose is the ratio of pmoles of incorporated carbon-14 to tritium labeled sugars in the gum fractions.

In the presence of all three sugar constituents, the ratio of glucose:mannose was 1.0:1, as expected for xanthan gum. When UDP-glucuronic acid was absent, the ratio was 2.1:1. See Table 1. This ratio is consistent with the hypothesis that the polysaccharide polymer is formed of trimer units which are intermediates in the xanthan gum biosynthetic pathway.

A pulse-chase in vitro experiment showed that lipid-linked cellobiose (a glucose dimer) was processed to lipid-linked trimer (glucose-glucose-mannose) and subsequently to polytrimer gum. A freeze-thaw lysate of strain B1459 S4-L was prepared as described above. UDP-[$^{14}$C]glucose was added to the lysate, comprising the "pulse", and radiolabeled cellobiose accumulated on the lipid carrier during an incubation of 13 minutes. The "chase" consisted of addition of 100-fold excess unlabeled UDP-glucose as well as GDP-[$^3$H]mannose. Aliquots of the incubation mixture of lysate and sugar nucleotides were removed at various times and processed to produce an organic extract (lipid carrier-linked fraction) and an aqueous fraction (containing gum). The oligosaccharides of the organic extract were acid hydrolyzed from the lipid carrier, dephosphorylated, separated by thin layer chromatography, removed from the chromatograms and the radiolabel quantitated. The results are shown in Table 2.

TABLE 2

Fate of UDP-[$^{14}$C] glucose in pulse-chase in vitro experiment with cell lysates of B1459 S4-L

| Pulse (12 min) | 9 pmol | Lipid-linked cellobiose |
|---|---|---|
| Chase (4 min) | 1 pmol | Lipid-linked cellobiose |
| | 10 pmol | Lipid-linked trimer |
| Chase (16 min) | 0.5 pmol | Lipid-linked cellobiose |
| | 6 pmol | Lipid-linked trimer |
| | 3 pmol | Soluble polytrimer |
| Chase (48 min) | 0.2 pmol | Lipid-linked cellobiose |
| | 0.4 pmol | Lipid-linked trimer |
| | 10 pmol | Soluble polytrimer |

The experimental conditions and the processing of the organic fraction and the soluble gum fraction are described in the text of Example 1.

The labeled glucose from UDP-[$^{14}$C]glucose, as can be seen in Table 2, was immediately incorporated into lipid-linked cellobiose in the "pulse". Upon addition of GDP-mannose and excess UDP-glucose (the chase), the labeled cellobiose was converted rapidly to labeled lipid-linked trimer, which was later detected as polytrimer gum in the aqueous fraction, at about 16 minutes after the chase began. This demonstrates the precursor-product relationships of UDP-glucose, lipid-linked cellobiose, lipid-linked trimer, and polytrimer gum, and their relationships to the xanthan biosynthetic pathway.

EXAMPLE 2

This example demonstrates the molar ratio of glucose to mannose in polytrimer gum synthesized in vitro by a glycosyltransferase IV-deficient mutant.

The method of preparing the lysate is described above in Example 1. The strain used to prepare the lysate was that designated ATCC No. 53195. Added to the lysate were either 1, 2 or 3 nucleotide-charged sugars, consisting of UDP-[$^{14}$C]glucose alone, UDP-[$^{14}$C]glucose and GDP-[$^3$H]mannose, or UDP-[$^{14}$C]glucose, GDP-[$^3$H]mannose and unlabeled UDP-glucuronic acid. At 30 minutes after addition of the sugar substrates, the aqueous fraction was processed and analyzed as described in Example 1. Results are shown in Table 3. When two sugar substrates, UDP-glucose and GDP-mannose, were present in the incubation mixture the molar ratio of glucose to mannose found in the gum was 2.4:1. When all three sugar substrates was incubated together with the lysate, the resulting gum had a 2.3:1 molar ratio of glucose to mannose.

TABLE 3

Incorporation of labeled sugars by freeze-thaw cell lysate of ATCC No. 53195 into polytrimer gum

| Reaction Mix | Gum Fraction (pmol) | | |
|---|---|---|---|
| | [$^3$H]man | [$^{14}$C]glc | glc/man |
| +2 UDPG, GDPM | 71 | 174 | 2.4 |
| +3 UDPG, GDPM, UDP-GA | 65 | 152 | 2.3 |
| dpm/pmol $^3$H = 340 | | | |

TABLE 3-continued

Incorporation of labeled sugars by freeze-thaw cell lysate of ATCC No. 53195 into polytrimer gum

| Reaction Mix | Gum Fraction (pmol) | | |
|---|---|---|---|
| | [$^3$H]man | [$^{14}$C]glc | glc/man |
| $^{14}$C = 40 | | | |

Abbreviations are explained in legend to Table 1.
Cell lysates of ATCC No. 53195 were incubated at 20° C. for 30 minutes in the reaction mixes indicated and processed to give the gum fractions as described in Example 1. The molar ratio of glucose to mannose indicated is the ratio of pmoles of incorporated carbon-14 to tritium labeled sugars in the processed fractions.

The presence of UDP-glucuronic acid has no effect on the ratio of glucose to mannose incorporated into a polysaccharide polymer when the cell-free lysate used is from a glycosyltransferase IV-deficient mutant. The biochemical phenotype of the mutant lysate when incubated with all three sugars is analogous to that of the wild-type lysate when incubated with only two sugar substrates, in that the in vitro produced gums both have a molar ratio of approximately 2:1 of glucose to mannose moieties.

EXAMPLE 3

This example demonstrates that the trimeric intermediate which is polymerized to form polytrimer gum has the same anomeric configuration of the sugars as in xanthan gum. In addition it demonstrates that the mannose of the trimer is attached to the non-reducing glucose of cellobiose in the lipid-linked intermediate.

Alpha-mannosidase (EC 3.2.1.24) and beta-glucosidase (EC 3.2.1.21) were used to singly or sequentially treat the trimeric oligosaccharide which had been synthesized and double labeled in vitro as described in Example 1. Alpha-mannosidase will hydrolyze terminal, unsubstituted mannose residues attached through an alpha-1 linkage. Beta-glucosidase will hydrolyze terminal, unsubstituted D-glucosyl residues attached in a beta-1 linkage.

The trimer was removed from the lipid and dephosphorylated. This was then deacetylated by base treatment, such as pH12 for 2 to 3 hours, because alpha-mannosidase cannot recognize acetylated mannose moieties.

The results were as follows. Treatment of trimeric oligosaccharide with beta-glucosidase left it unchanged. When alpha-mannosidase was used to treat the trimeric oligosaccharide, cellobiose and mannose were formed. When the trimeric oligomer was treated with alpha-mannosidase, first, and beta-glucosidase, second, glucose and mannose were formed. The results confirm that mannose is attached to the non-reducing glucose by an alpha-linkage in the trimeric intermediate, and that the glucose moieties are beta-linked. This confirms that trimer is an intermediate product of the normal xanthan enzyme pathway.

EXAMPLE 4

This example shows the methods of mutagenesis and screening which were employed to generate the mutant strains which are xanthan gum deficient due to a lesion in the gene for glycosyltransferase IV.

*Xanthomonas campestris*, genetically marked with a chromosomal resistance to streptomycin, was used as a recipient in a conjugation with *E. coli* LE392 containing plasmid pRK2013::Tn10. Plasmid pRK2013 contains Tn903 which encodes kanamycin resistance, (Figurski, D. H., and Helinski, D. R., Proc. Natl. Acad. Sci., U.S.A., 76, 1648-1652 (1979),) and the plasmid cannot replicate in Xanthomonas, (Ditta, G., et al., supra.) Transposon Tn10 encodes resistance to tetracycline. Transconjugants were selected which were resistant to streptomycin and kanamycin, or streptomycin and tetracycline. The former occurred at a frequency of about $4 \times 10^{-6}$/recipient and presumably resulted from a transposition of Tn903. The latter occurred at a frequency of about $3 \times 10^{-6}$/recipient and presumably resulted from a transposition of Tn10 into the genome of *Xanthomonas campestris*.

Auxotrophs were found among these transconjugants at a frequency of about 2%; their needs were widely distributed among the various nutritional requirements. This indicates that these transposons do not have a particularly preferred locus for insertion in Xanthomonas. Prototrophic revertants of the auxotrophs were selected, and most were found to be drug-sensitive; this suggests that the auxotrophies were caused by transposon insertion.

To screen for xanthan gum deficient mutants among the doubly resistant transconjugants, Congo Red dye, which enhances the morphological distinction between xanthan gum producing and nonproducing colonies, was added to the solid media. Colonial morphology was examined after 7 to 12 days incubation at 30° C. Xanthan gum deficient mutants were found at a frequency of approximately $10^{-4}$.

To identify a glycosyltransferase IV mutant from among the xanthan gum deficient mutants, freeze-thaw lysates of each were prepared. Radiolabeled UDP-glucose and GDP-mannose were added with or without UDP-glucuronic acid. The desired mutants made a gum having a glucose:mannose ratio of about 2:1, irrespective of the presence of UDP-glucuronic acid. Several mutants were found of this description. They contain lesions due to Tn10 insertion. Mutants induced by Tn903 were also found having this phenotype. In addition mutants have been isolated having this phenotype which were induced by nitrosoguanidine.

EXAMPLE 5

This example demonstrates the use of a glycosyltransferase IV deficient mutant to produce polytrimer gum in vivo.

To obtain in vivo synthesized gums, five liters each of wild-type NRRL B-1459 S4-L and the glycosyltransferase IV deficient mutant of Example 4 (ATCC No. 53195) were aerobically grown in a fermenter at 28° C. to 32° C., with the pH controlled at pH 6.0 to 8.0. A minimal medium was used containing 10 g/l potassium phosphate, 1.43 g/l ammonium sulfate, 2 g/l citric acid, 30 g/l glucose, and trace elements. After 145 hours, the gums were recovered and purified. The cells were removed by centrifugation and the gums precipitated from the broth by addition of isopropanol (55% v/v) and sodium chloride (0.5% w/v). the precipitates were collected by filtration and redissolved in water. The gums were reprecipitated with isopropanol (55% v/v) without salt and redissolved in water. The preparations were dialyzed using 12,000 MW cutoff membrane dialysis tubing against water for three days.

The glucose:mannose ratios were determined by complete acid hydrolysis of the polysaccharide polymers with subsequent analysis by high performance liquid chromatography (HPLC), and found to conform to the ratios found for the in vitro synthesized polymers. The glycosyltransferase IV deficient mutant designated ATCC No. 53195 made a gum with a glucose to mannose ratio of about 2.15:1, whereas the wild-type made a gum of ratio about 0.96:1.

Other in vivo produced samples of polytrimer gum were assayed by HPLC or by enzymatic analyses of the sugars after acid hydrolysis. For the twenty-four analyses performed, the molar ratios range from 1.43:1 to 2.44:1 of glucose to mannose. The mean ratio was 1.90±0.15:1 for polytrimer made by the glycosyltransferase IV deficient mutant strain.

Also shown by the HPLC analysis of the in vivo produced polytrimer within detectable limits were 1-the absence of glucuronic acid; 2-the absence of pyruvate; 3-the presence of acetate; 4-the absence of sugars other than glucose and mannose.

EXAMPLE 6

This example shows that polytrimer provides aqueous solutions which exhibit improved rheological properties compared to xanthan gum over a range of temperatures and inorganic salt concentrations.

Figure 2:
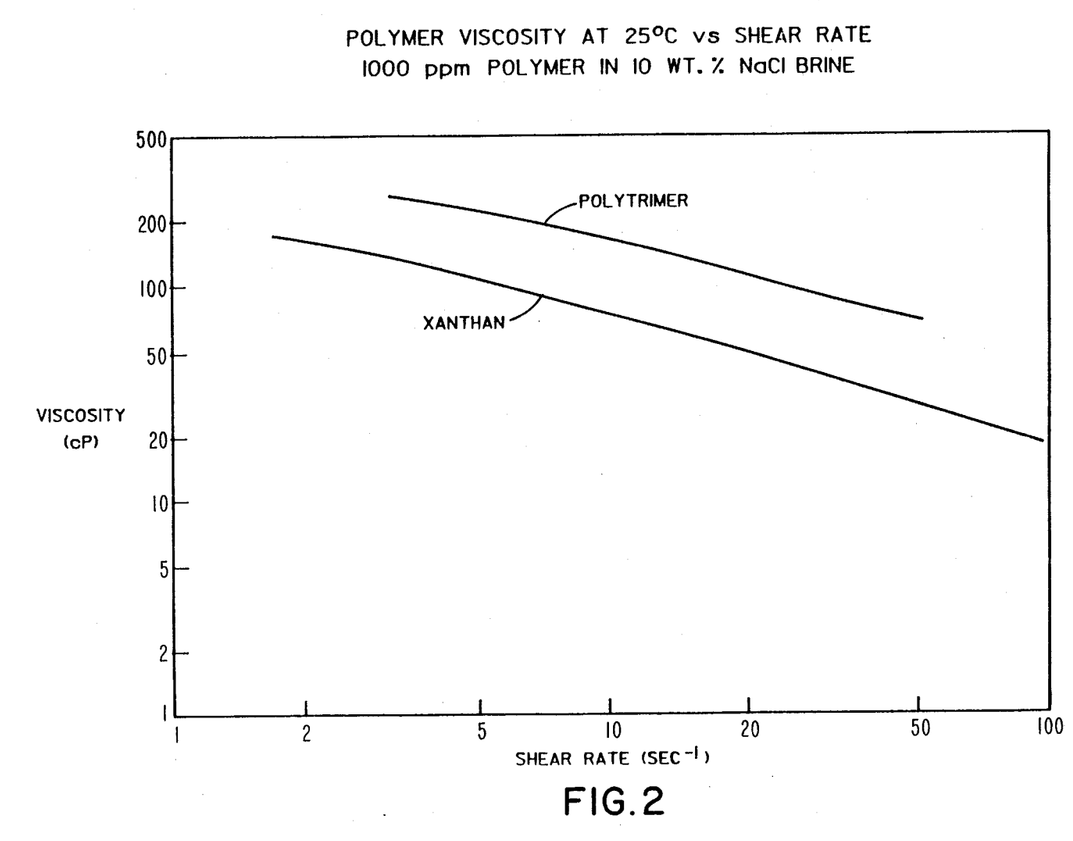
FIG. 2 shows the viscosities of solutions of polytrimer and xanthan gum, each at 1000 ppm in 10 weight percent NaCl brine, as a function of shear rate.

Solutions of polytrimer gum (synthesized in vivo in accordance with Example 5) and xanthan gum (purified Pfizer Flocon 4800, were prepared at a concentration of 1,000 ppm in a water containing 10 weight percent sodium chloride. Polytrimer gum shows substantially greater viscosity than xanthan gum over a wide range of shear rates (FIG. 2).

Figure 3:
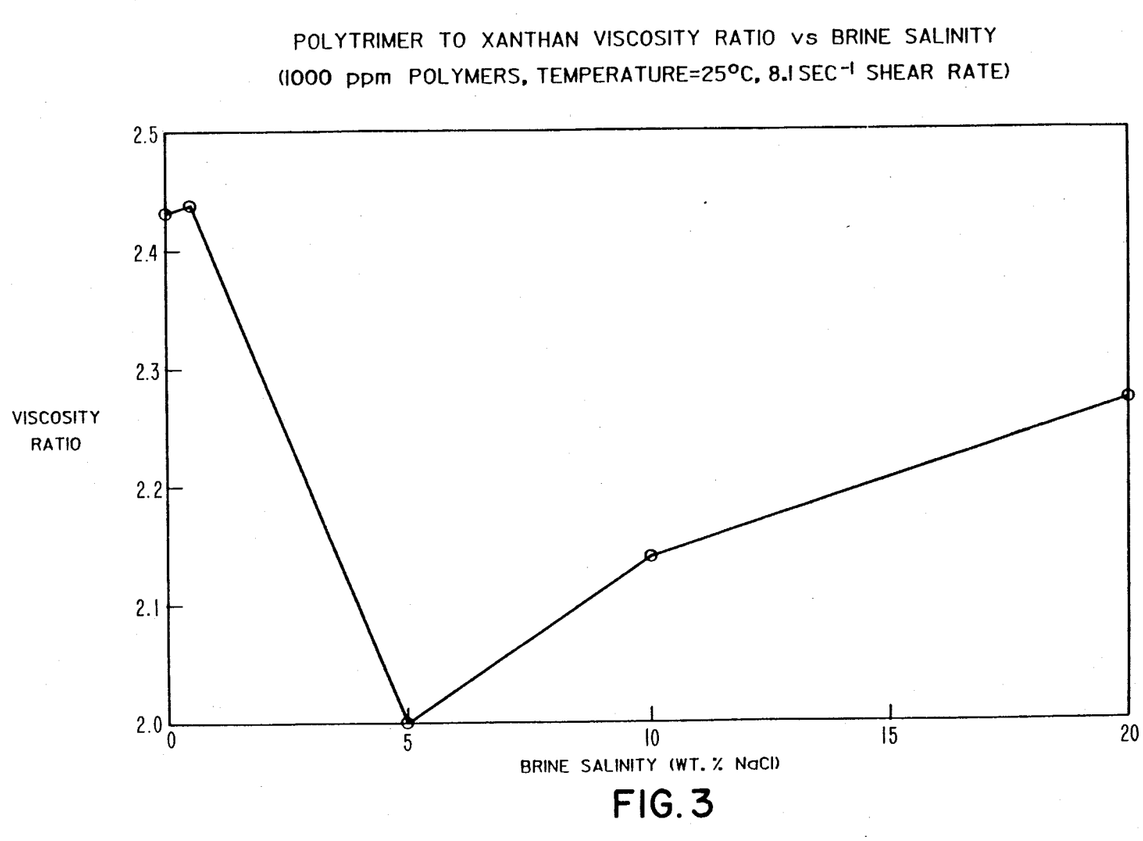
FIG. 3 shows the ratio of viscosities of solutions of 1,000 ppm polytrimer to xanthan gum as a function of brine salinity.
Figure 4:
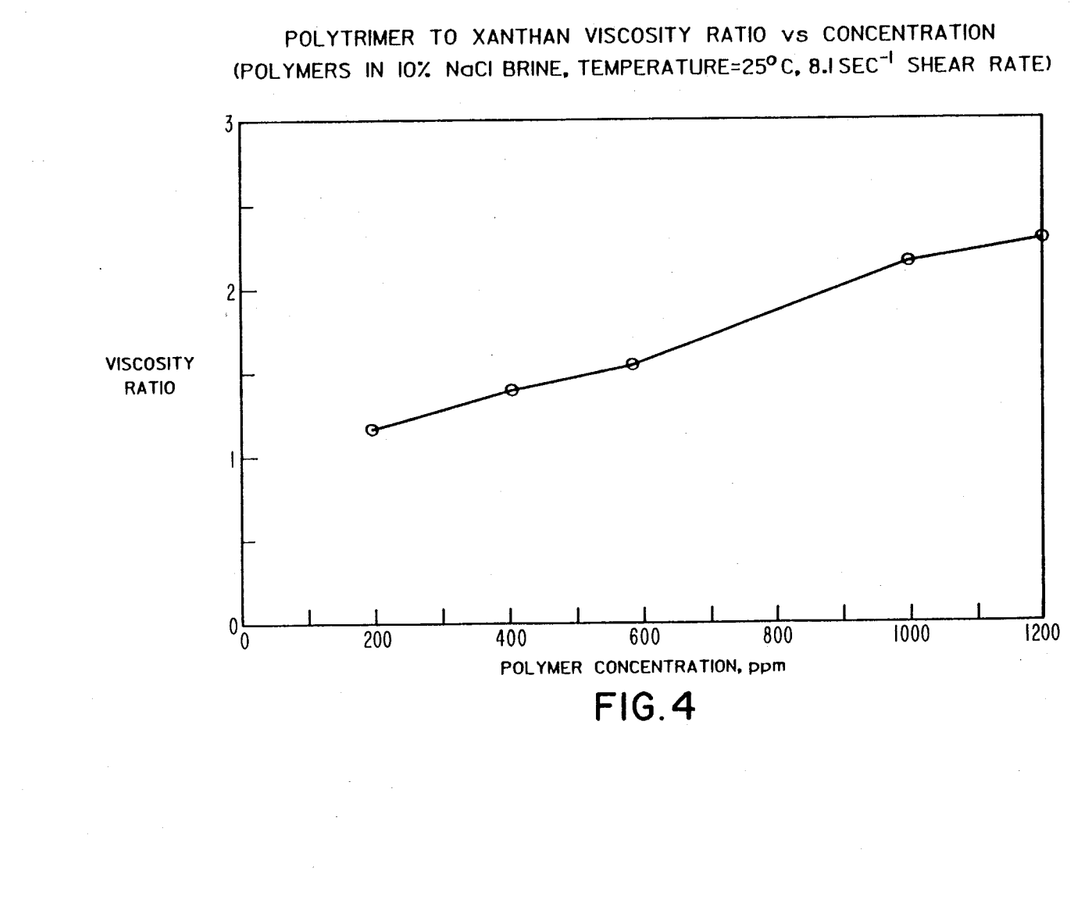
FIG. 4 shows the ratio of viscosities of solutions of polytrimer to xanthan gum as a function of polymer concentration in 10 weight percent NaCl brine.
Figure 5:
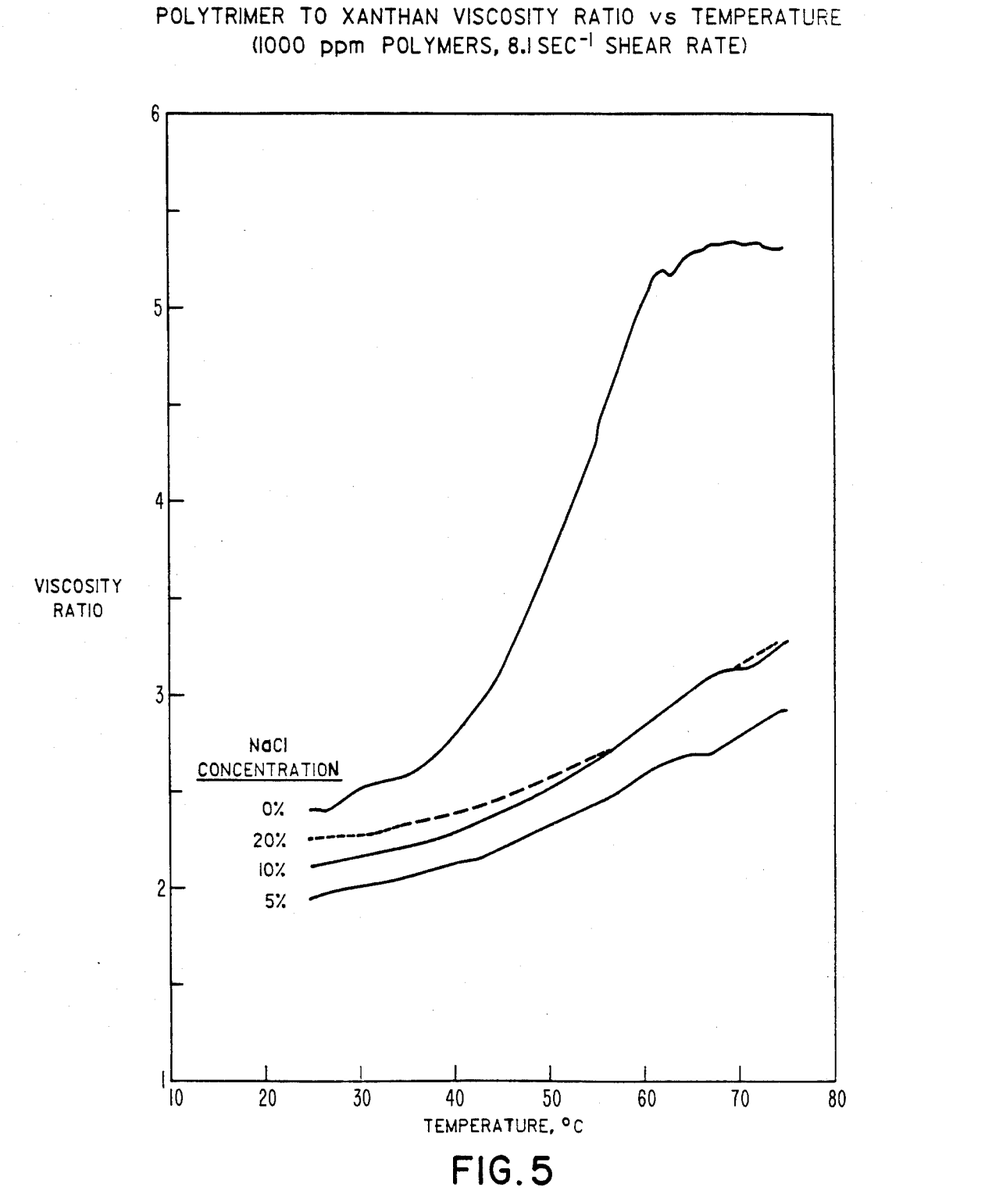
FIG. 5 shows the ratio of viscosities of solutions of 1,000 ppm polytrimer to xanthan gum as a function of temperature in brines of various salinities.

The ratio of polytrimer to xanthan viscosity at room temperature varies with water salinity and is between 2 and 2.5 over a salinity range of 0 to 20 weight percent sodium chloride, as shown in FIG. 3. The ratio of polytrimer viscosity to xanthan viscosity also varies with polymer concentration (FIG. 4). Finally, the improvement in polytrimer viscosity over xanthan viscosity increases with temperature over a range of 25° to 75° C., for water salinities of 0 to 20 weight percent sodium chloride (FIG. 5).

Since variations of this invention will be apparent to those skilled in the art, it is intended that this invention be limited only by the scope of the claims.

We claim:

1. Water-soluble, polysaccharide polymer consisting essentially of glucose and mannose moieties, having D-glucose:D-mannose ratio of about 2:1, wherein the D-glucose moieties are linked in a beta-[1,4] configuration, and the D-mannose moieties are linked in an alpha-[1,3] configuration, generally to alternate glucose moieties.

2. The polymer of claim 1 wherein the mannose moieties of the polysaccharide polymer are acetylated at the 6-O position.

3. The polymer of claim 1 wherein the mannose moieties of the polysaccharide polymer are not acetylated at the 6-O position.

4. A composition comprising a water-soluble, polysaccharide polymer consisting essentially of glucose and mannose moieties, having D-glucose:D-mannose ratio of about 2:1, wherein the D-glucose moieties are linked in a beta-[1,4] space configuration, and the D-mannose moieties are linked in an alpha-[1,3] configuration, generally to alternate glucose moieties, wherein the polysaccharide polymer is present in aqueous solution in amounts greater than about 1% by weight.

5. A composition comprising a water-soluble, polysaccharide polymer consisting essentially of glucose and mannose moieties, having D-glucose:D-mannose ratio of about 2:1, wherein the D-glucose moieties are linked in a beta-[1,4] space configuration, and the D-mannose moieties are linked in an alpha-[1,3] configuration, generally to alternate glucose moieties, wherein the composition is an aqueous solution containing at least 0.001% by weight of said water soluble, polysaccharide polymer.

* * * * *